(12) United States Patent  (10) Patent No.: US 8,071,828 B2
Cao et al.  (45) Date of Patent: Dec. 6, 2011

(54) TRANSALKYLATION OF HEAVY AROMATIC HYDROCARBON FEEDSTOCKS

(75) Inventors: Chunshe Cao, Houston, TX (US); Michel Molinier, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 12/973,331

(22) Filed: Dec. 20, 2010

(65) Prior Publication Data

US 2011/0190560 A1    Aug. 4, 2011

Related U.S. Application Data

(60) Provisional application No. 61/301,072, filed on Feb. 3, 2010.

(51) Int. Cl.
*C07C 6/12* (2006.01)
*C07C 4/18* (2006.01)
*C07C 4/20* (2006.01)

(52) U.S. Cl. ......... 585/319; 585/475; 585/488; 585/489

(58) Field of Classification Search ............ 585/319, 585/475, 489, 488
See application file for complete search history.

(56) References Cited

U.S. PATENT DOCUMENTS

| | | | |
|---|---|---|---|
| 5,030,787 | A | 7/1991 | Absil et al. |
| 5,942,651 | A | 8/1999 | Beech, Jr. et al. |
| 7,663,010 | B2 * | 2/2010 | Levin .................. 585/475 |
| 2009/0112034 | A1 | 4/2009 | Levin |

OTHER PUBLICATIONS

Tsai et al., "*Reactivation of Acidic Sites 1-15 in Mordenite Used in Toluene Disproportionation*", Applied Catalysis A: General, Elsevier Science, Amsterdam, 2006, pp. 292-298.

* cited by examiner

*Primary Examiner* — Thuan Dinh Dang

(74) *Attorney, Agent, or Firm* — Andrew B. Griffis

(57) ABSTRACT

In a process for producing xylene by transalkylation of a $C_9+$ aromatic hydrocarbon feedstock, the feedstock, at least one $C_6$-$C_7$ aromatic hydrocarbon and hydrogen are supplied to at least one reaction zone containing at least first and second catalyst beds located such that the feedstock and hydrogen contact the first bed before contacting the second bed. The first catalyst bed comprises a first catalyst composition comprising a molecular sieve having a Constraint Index in the range of about 3 to about 12 and at least one metal or compound thereof of Groups 6-10 of the Periodic Table of the Elements, and the second catalyst bed comprises a second catalyst composition comprising a molecular sieve having a Constraint Index less than 3. The at least one reaction zone is operated under a first set of conditions effective to (i) dealkylate aromatic hydrocarbons in the feedstock containing $C_2+$ alkyl groups and to saturate $C_2+$ olefins formed in the first catalyst bed and (ii) transalkylate $C_9+$ aromatic hydrocarbons with said $C_6$-$C_7$ aromatic hydrocarbon to produce xylene in the second catalyst bed. Periodically the supply of the feedstock and said at least one $C_6$-$C_7$ aromatic hydrocarbon, but not the hydrogen, to said at least one reaction zone is interrupted and the first and second catalyst compositions are contacted with the hydrogen under a second set of conditions effective to enhance the activity of the first and second catalyst compositions.

5 Claims, 4 Drawing Sheets

TRANSALKYLATION OF HEAVY AROMATIC HYDROCARBON FEEDSTOCKS

CROSS REFERENCE TO RELATED APPLICATIONS

This application claims priority to U.S. Provisional Application Ser. No. 61/301,072 filed Feb. 3, 2010, the disclosure of which is fully incorporated herein by reference.

FIELD

This invention relates to transalkylation of heavy ($C_9+$) aromatic hydrocarbon feedstocks to produce xylene and either benzene or toluene.

BACKGROUND

An important source of xylene in an oil refinery is catalytic reformate, which is prepared by contacting a mixture of petroleum naphtha and hydrogen with a strong hydrogenation/dehydrogenation catalyst, such as platinum, on a moderately acidic support, such as a halogen-treated alumina. Usually, a $C_6$ to $C_8$ fraction is separated from the reformate and extracted with a solvent selective for aromatics or aliphatics to produce a mixture of aromatic compounds that is relatively free of aliphatics. This mixture of aromatic compounds usually contains benzene, toluene and xylenes (BTX), along with ethylbenzene.

However, the quantity of xylene available from reforming is limited and so recently refineries have also focused on the production of xylene by transalkylation of $C_9+$ aromatic hydrocarbons with benzene and/or toluene over noble metal-containing zeolite catalysts. One such process, using MCM-22 as the zeolite catalyst is disclosed in U.S. Pat. No. 5,030,787. However, during the transalkylation of $C_9+$ aromatics with, for example, toluene to produce xylene and benzene, saturated by-products, which boil in the same temperature range as the desired aromatic products, are typically produced making separation of the desired products at high purity levels difficult. For example, a commercial benzene product may need a purity of 99.85 wt % or higher. However, initial benzene purity after distillation of a transalkylation reaction product is typically only 99.2% to 99.5% due to the presence of coboilers, such as methylcyclopentane, cyclohexane, 2,3-dimethylpentane, dimethylcyclopentane and 3-methylhexane. Therefore, an additional extraction step is usually required to further improve benzene product purity to the desired level.

One solution to the problem of the production of benzene co-boilers during the transalkylation of heavy aromatics is disclosed in U.S. Pat. No. 5,942,651 and involves the steps of contacting a feed comprising $C_9+$ aromatic hydrocarbons and toluene under transalkylation reaction conditions with a first catalyst composition comprising a zeolite having a Constraint Index ranging from 0.5 to 3, such as ZSM-12, and a hydrogenation component. The effluent resulting from the first contacting step is then contacted with a second catalyst composition which comprises a zeolite having a Constraint Index ranging from 3 to 12, such as ZSM-5, and which may be in a separate bed or a separate reactor from the first catalyst composition to produce a transalkylation reaction product comprising benzene and xylene. A benzene product having a purity of at least 99.85% may be obtained by distilling the benzene from the transalkylation reaction product, without the need for an additional extraction step. According to the '651 patent, the second catalyst composition comprises up to 20 wt % of the total weight of the first and second catalyst compositions.

Another problem associated with heavy aromatics alkylation processes is catalyst aging since, as the catalyst loses activity with increasing time on stream, higher temperatures are normally required to maintain constant conversion. When the maximum reactor temperature is reached, the catalyst needs to be replaced or regenerated, normally by oxidation. Depending on the $C_9+:C_6$ or $C_7$ composition of the feed, the cycle length may vary from only 9 months for high $C_9+:C_7$ ratios of 85:15 to about 5 years for low $C_9+:C_7$ ratios of 20:80. Recent work has shown that the aging rate of existing transalkylation catalysts is also strongly dependent on the presence in the feed of aromatic compounds having alkyl substituents with two or more carbon atoms, such as ethyl and propyl groups. Thus these compounds tend to undergo disproportionation to produce $C_{10}+$ coke precursors.

To address the problem of $C_9+$ feeds containing high levels of ethyl and propyl substituents, U.S. Published Application No. 2009/0112034 discloses a catalyst system adapted for transalkylation of a $C_9+$ aromatic feedstock with a $C_6$-$C_7$ aromatic feedstock comprising: (a) a first catalyst comprising a first molecular sieve having a Constraint Index in the range of 3-12 and 0.01 to 5 wt % of at least one source of a first metal element of Groups 6-10; and (b) a second catalyst comprising a second molecular sieve having a Constraint Index less than 3 and 0 to 5 wt % of at least one source of a second metal element of Groups 6-10, wherein the weight ratio of said first catalyst to said second catalyst is in the range of 5:95 to 75:25. The first catalyst, which is optimized for dealkylation of the ethyl and propyl groups in the feed, is located in front of said second catalyst, which is optimized for transalkylation, when they are brought into contact with said $C_9+$ aromatic feedstock and said $C_6$-$C_7$ aromatic feedstock in the presence of hydrogen.

However, although the multiple catalyst bed system of U.S. Published Application No. 2009/0112034 allows significantly increased cycle lengths over single catalyst bed processes in the transalkylation of heavy aromatic feeds, it is still inherently subject to catalyst deactivation albeit at a reduced rate. Thus, even with a multiple catalyst bed system, there remains a need to extend catalyst life and thereby decrease operation downtime. According to the present invention, it has now been found that periodically treating a multiple bed transalkylation catalyst with hydrogen gas in-situ reduces the formation of coke precursors and helps maintain catalyst activity.

SUMMARY

In one aspect, the invention resides in a process for producing xylene by transalkylation of a $C_9+$ aromatic hydrocarbon feedstock, the process comprising:

(a) supplying the feedstock, at least one $C_6$-$C_7$ aromatic hydrocarbon and hydrogen to at least one reaction zone containing at least first and second catalyst beds located such that the feedstock and hydrogen contact the first bed before contacting the second bed, wherein the first catalyst bed comprises a first catalyst composition comprising a molecular sieve having a Constraint Index in the range of about 3 to about 12 and at least one metal or compound thereof of Groups 6-10 of the Periodic Table of the Elements, and wherein the second catalyst bed comprises a second catalyst composition comprising a molecular sieve having a Constraint Index less than 3;

(b) with the feedstock, $C_6$-$C_7$ aromatic hydrocarbon and hydrogen being supplied to said at least one reaction zone, operating said reaction zone(s) under a first set of conditions effective to (i) dealkylate aromatic hydrocarbons in the feedstock containing $C_2$+ alkyl groups and to saturate $C_2$+ olefins formed in the first catalyst bed and (ii) transalkylate $C_9$+ aromatic hydrocarbons with said $C_6$-$C_7$ aromatic hydrocarbon to produce xylene in the second catalyst bed; and (c) periodically interrupting the supply of the feedstock and said at least one $C_6$-$C_7$ aromatic hydrocarbon, but not the hydrogen, to said at least one reaction zone and contacting the first and second catalyst compositions with said hydrogen under a second set of conditions effective to enhance the activity of said first and second catalyst compositions.

Conveniently, said at least one metal of the first catalyst composition comprises at least one of platinum, palladium, iridium, and rhenium and is present in said first catalyst composition in an amount between about 0.01 and about 5 wt % of the catalyst composition.

In one embodiment, said first catalyst composition comprises at least one further metal or compound thereof of Groups 6 to 10 of the Periodic Table of the Elements, such as copper, zinc and/or tin. Conveniently, said at least one further metal is present in its respective catalyst composition in an amount between about 0.01 and about 1 wt % of the catalyst composition.

Conveniently, said first molecular sieve comprises at least one of ZSM-5, ZSM-11, ZSM-22, ZSM-23, ZSM-35, and ZSM-48 and has an alpha value in the range of 100 to 1500.

Conveniently, said second molecular sieve comprises at least one of zeolite beta, zeolite Y, Ultrastable Y (USY), Dealuminized Y (Deal Y), mordenite, NU-87, ZSM-3, ZSM-4 (Mazzite), ZSM-12, ZSM-18, MCM-22, MCM-36, MCM-49, MCM-56, EMM-10, EMM-10-P and ZSM-20 and has an alpha value in the range of 20 to 500.

Conveniently, the weight ratio of the first catalyst composition to the second catalyst composition is in the range of 5:95 to 75:25.

Conveniently, said at least one reaction zone contains a third catalyst bed located such that the feedstock and hydrogen in (a) and (b) contact the third bed after contacting the second bed, wherein the third catalyst bed comprises a third catalyst composition comprising a molecular sieve having a Constraint Index in the range of about 1 to about 12 and effective under said first conditions effective to crack non-aromatic cyclic hydrocarbons.

Conveniently, said $C_9$+ aromatic hydrocarbon feedstock and said at least one $C_6$-$C_7$ aromatic hydrocarbon are supplied to said at least one reaction zone in (a) and (b) in a molar ratio of about 0.08:1 to about 6.8:1.

Conveniently, hydrogen, said $C_9$+ aromatic hydrocarbon feedstock and said at least one $C_6$-$C_7$ aromatic hydrocarbon are supplied to said at least one reaction zone in (a) and (b) so that the a molar ratio of hydrogen to total hydrocarbon is about 0.5:1 to about 6:1.

In one embodiment, the first conditions comprise a temperature in the range of about 360 to about 500° C., a pressure in the range of about 790 to about 6000 kPa-a, and a WHSV in the range of about 0.01 to about 10 $hr^{-1}$.

In another embodiment, the second conditions comprise a temperature in the range of about 365 to about 500° C., a pressure in the range of about 150 to about 6000 kPa-a, and a WHSV in the range of about 0.01 to about 10 $hr^{-1}$.

Conveniently, the ratio of the time during which the feedstock, $C_6$-$C_7$ aromatic hydrocarbon and hydrogen are supplied to said at least one reaction zone under the first set of conditions in (b) and the time during which hydrogen is supplied to said at least one reaction zone under the second set of conditions in (c) is in the range from about 1:1 to about 500:1.

DETAILED DESCRIPTION

Figure 1:
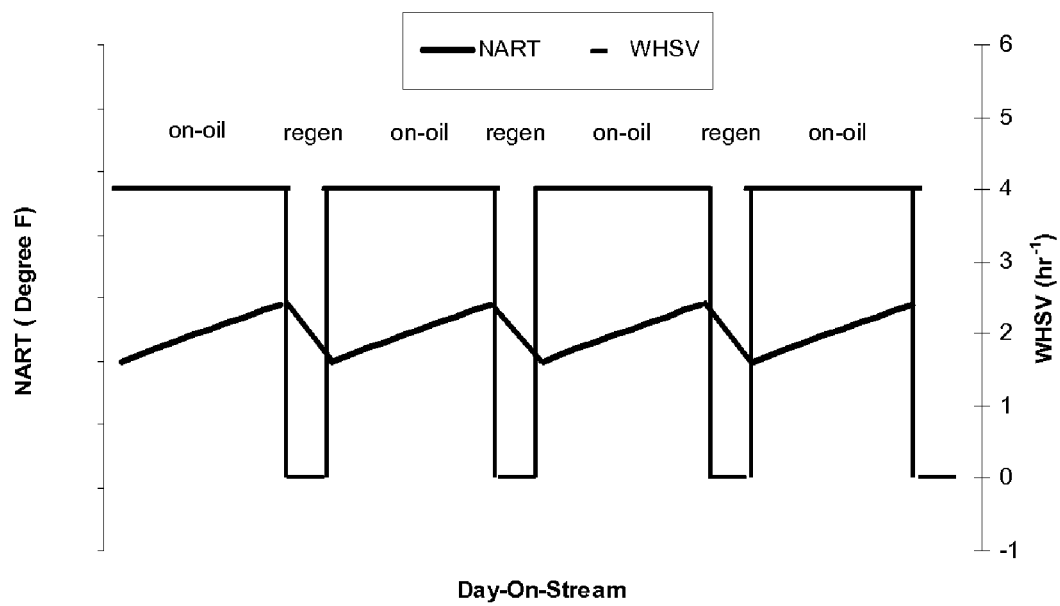
FIG. 1 is a graph of normalized average reactor temperature (NART) and hydrocarbon WHSV against days on stream for a typical transalkylation process as described herein.

Described herein is a process for operating and in situ regenerating a multi-bed catalyst system for producing xylene from a heavy ($C_9$+) aromatic hydrocarbon feedstock. In the process, the $C_9$+ aromatic hydrocarbon feedstock, a $C_6$-$C_7$ aromatic hydrocarbon and hydrogen are supplied to one or more reaction zones which contain the catalyst system and which are operated under a first set of conditions effective to transalkylate $C_9$+ aromatic hydrocarbons with the $C_6$-$C_7$ aromatic hydrocarbon to produce xylene. Periodically, as the catalyst system loses its activity, the supply of the feedstock and the $C_6$-$C_7$ aromatic hydrocarbon, but not the hydrogen, is interrupted and the catalyst system is contacted with the hydrogen under a second set of conditions effective to enhance the activity of the catalyst system.

Feedstocks

As used herein the term "$C_n$+", wherein n is a positive integer, means a compound or group containing at least n carbon atoms. In addition, the term "$C_n$+ aromatic hydrocarbon feedstock", wherein n is a positive integer, means that a feedstock comprising greater than 20 wt % of aromatic hydrocarbons having at least n number of carbon atom(s) per molecule.

Thus the heavy aromatic feedstock used in the present process comprises greater than 20 wt %, conveniently at least 40 wt %, typically at least 50 wt %, often at least 80 wt % or even at least 90 wt % of one or more aromatic compounds containing at least 9 carbon atoms. Specific $C_9$+ aromatic compounds found in a typical feed include mesitylene (1,3,5-trimethylbenzene), durene (1,2,4,5-tetramethylbenzene), hemimellitene (1,2,4-trimethylbenzene), pseudocumene (1,2,4-trimethylbenzene), ethyltoluenes, ethylxylenes, propyl-substituted benzenes, butyl-substituted benzenes, and dimethylethylbenzenes. Suitable sources of the $C_9$+ aromatics are any $C_9$+ fraction from any refinery process that is rich in aromatics, such as catalytic reformate, FCC naphtha or TCC naphtha.

The feed to the process also includes benzene and/or toluene, typically toluene. The feed may also include unreacted toluene and $C_9$+ aromatic feedstock that is recycled after separation of the xylene product from the effluent of the transalkylation reaction. Typically, the $C_6$ and/or $C_7$ aromatic hydrocarbon constitutes up to 90 wt %, such as from 10 to 70 wt % of the entire feed, whereas the $C_9$+ aromatics component constitutes at least 10 wt %, such as from 30 to 85 wt %, of the entire feed to the transalkylation reaction.

The feedstock may be characterized by the molar ratio of methyl groups to single aromatic rings. In some embodiments, the combined feedstock (the combination of the $C_9+$ and the $C_6$-$C_7$ aromatic feedstocks) has molar ratio of methyl groups to single aromatic rings in the range of from 0.5 to 4, such as from 1 to 2.5, for example from 1.5 to 2.25.

First Catalyst Bed

The first catalyst bed employed in the present catalyst system accommodates a first catalyst comprising a first molecular sieve having a Constraint Index in the range of about 3 to about 12 and at least first and second different metals or compounds thereof of Groups 6 to 12 of the Periodic Table of the Elements.

Constraint Index is a convenient measure of the extent to which an aluminosilicate or other molecular sieve provides controlled access to molecules of varying sizes to its internal structure. For example, molecular sieves which provide a highly restricted access to and egress from its internal structure have a high value for the Constraint Index. Molecular sieves of this kind usually have pores of small diameter, e.g., less than 5 Angstroms. On the other hand, molecular sieves which provide relatively free access to their internal pore structure have a low value for the Constraint Index, and usually pores of large size. The method by which Constraint Index is determined is described fully in U.S. Pat. No. 4,016,218, which is incorporated herein by reference for the details of the method.

Suitable molecular sieves for use in the first catalyst comprise at least one of ZSM-5, ZSM-11, ZSM-22, ZSM-23, ZSM-35, ZSM-48, ZSM-57 and ZSM-58. ZSM-5 is described in detail in U.S. Pat. No. 3,702,886 and RE. 29,948. ZSM-11 is described in detail in U.S. Pat. No. 3,709,979. ZSM-22 is described in U.S. Pat. Nos. 4,556,477 and 5,336,478. ZSM-23 is described in U.S. Pat. No. 4,076,842. ZSM-35 is described in U.S. Pat. No. 4,016,245. ZSM-48 is more particularly described in U.S. Pat. Nos. 4,234,231 and 4,375,573. ZSM-57 is described in U.S. Pat. No. 4,873,067. ZSM-58 is described in U.S. Pat. No. 4,698,217.

In one preferred embodiment, the first molecular sieve comprises ZSM-5 and especially ZSM-5 having an average crystal size of less than 0.1 micron, such as about 0.05 micron.

Conveniently, the first molecular sieve has an alpha value in the range of about 100 to about 1500, such as about 150 to about 1000, for example about 300 to about 600. Alpha value is a measure of the cracking activity of a catalyst and is described in U.S. Pat. No. 3,354,078 and in the Journal of Catalysis, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the Journal of Catalysis, Vol. 61, page 395.

Generally, the first molecular sieve is an aluminosilicate having a silica to alumina molar ratio of less than 1000, typically from about 10 to about 100.

Typically, the first catalyst comprises at least 1 wt %, preferably at least 10 wt %, more preferably at least 50 wt %, and most preferably at least 65 wt %, of the first molecular sieve.

In addition to a molecular sieve having a Constraint Index in the range of about 3 to about 12, the first catalyst comprises at least a first metal, and generally first and second different metals, or compounds thereof of Groups 6 to 12 of the Periodic Table of the Elements. As used herein, the numbering scheme for the Periodic Table Groups is used as in Chemical and Engineering News, 63(5), 27 (1985).

The first metal is generally selected from platinum, palladium, iridium, rhenium and mixtures thereof, whereas the second metal, if present, is chosen so as to lower the benzene saturation activity of the first metal and is conveniently selected from at least one of copper, silver, gold, ruthenium, iron, tungsten, molybdenum, cobalt, nickel, tin and zinc. In one embodiment, the first metal comprises platinum and said second metal comprises copper.

Conveniently, the first metal is present in the first catalyst in amount between about 0.01 and about 5 wt % of the first catalyst and the optional second metal is present in the first catalyst in amount between about 0.01 and about 1 wt % of the first catalyst.

In most cases, the first catalyst also comprises a binder or matrix material that is resistant to the temperatures and other conditions employed in the present transalkylation process. Such materials include active and inactive materials and synthetic or naturally occurring zeolites, as well as inorganic materials such as clays, silica and/or metal oxides such as alumina. The inorganic material may be either naturally occurring, or in the form of gelatinous precipitates or gels including mixtures of silica and metal oxides. Use of a binder or matrix material which itself is catalytically active, may change the conversion and/or selectivity of the catalyst composition. Inactive materials suitably serve as diluents to control the amount of conversion so that transalkylated products can be obtained in an economical and orderly manner without employing other means for controlling the rate of reaction. These catalytically active or inactive materials may include, for example, naturally occurring clays, e.g., bentonite and kaolin, to improve the crush strength of the catalyst composition under commercial operating conditions.

Naturally occurring clays that can be composited with the first molecular sieve as a binder for the catalyst composition include the montmorillonite and kaolin family, which families include the subbentonites, and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the first molecular sieve can be composited with a porous matrix binder material, such as an inorganic oxide selected from the group consisting of silica, alumina, zirconia, titania, thoria, beryllia, magnesia, and combinations thereof, such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. It may also be advantageous to provide at least a part of the foregoing porous matrix binder material in colloidal form so as to facilitate extrusion of the catalyst composition.

Typically the first molecular sieve is admixed with the binder or matrix material so that the first catalyst composition contains the binder or matrix material in an amount ranging from 5 to 95 wt %, and typically from 10 to 60 wt %.

Second Catalyst Bed

The second catalyst bed accommodates a second catalyst comprising a second molecular sieve having a Constraint Index less than 3 and optionally one or more metals or compounds thereof of Groups 6 to 12 of the Periodic Table of the Elements.

Suitable molecular sieves for use in the second catalyst composition comprise at least one of zeolite beta, zeolite Y, Ultrastable Y (USY), Dealuminized Y (Deal Y), mordenite, NU-87, ZSM-3, ZSM-4 (Mazzite), ZSM-12, ZSM-18, MCM-22, PSH-3, SSZ-25, MCM-36, MCM-49, MCM-56, EMM-10, EMM-10-P and ZSM-20. Zeolite ZSM-4 is described in U.S. Pat. No. 3,923,636. Zeolite ZSM-12 is described in U.S. Pat. No. 3,832,449. Zeolite ZSM-20 is described in U.S. Pat. No. 3,972,983. Zeolite Beta is described in U.S. Pat. No. 3,308,069, and RE. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Rare earth exchanged Y (REY) is described in U.S. Pat. No. 3,524,820. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. MCM-22 is described in U.S. Pat. No. 4,954,325. PSH-3 is described in U.S. Pat. No. 4,439,409. SSZ-25 is described in U.S. Pat. No. 4,826,667. MCM-36 is described in U.S. Pat. No. 5,250,277. MCM-49 is described in U.S. Pat. No. 5,236,575. MCM-56 is described in U.S. Pat. No. 5,362,697.

In one preferred embodiment, the second molecular sieve comprises ZSM-12 and especially ZSM-12 having an average crystal size of less than 0.1 micron, such as about 0.05 micron.

Conveniently, the second molecular sieve has an alpha value of at least 20, such as from about 20 to about 500, for example from about 30 to about 100.

Generally, the second molecular sieve is an aluminosilicate having a silica to alumina molar ratio of less than 500, typically from about 50 to about 300.

Typically, the second catalyst comprises at least 1 wt %, preferably at least 10 wt %, more preferably at least 50 wt %, and most preferably at least 65 wt %, of the second molecular sieve.

Optionally, the second catalyst comprises at least one and preferably at least two metals or compounds thereof of Groups 6 to 12 of the Periodic Table of the Elements.

Generally, the second catalyst comprises the same first and second metals present in the same amounts as contained by the first catalyst.

Generally, the second catalyst also contains a binder or matrix material, which can be any of the materials listed as being suitable for the first catalyst and can be present in an amount ranging from 5 to 95 wt %, and typically from 10 to 60 wt %, of the second catalyst composition.

Conveniently, the weight ratio of the first catalyst to the second catalyst is in the range of 5:95 to 75:25.

Optional Third Catalyst Bed

In addition to the first and second catalyst beds employed in the present multi-bed catalysts system, it may be desirable to incorporate a third catalyst bed downstream of the second catalyst bed and effective to crack non-aromatic cyclic hydrocarbons in the effluent from the first and second catalyst beds. The third catalyst bed accommodates a third catalyst comprising a third molecular sieve having a Constraint Index from about 1 to 12. Suitable molecular sieves for use in the third catalyst comprise at least one of ZSM-5, ZSM-11, ZSM-12, zeolite beta, ZSM-22, ZSM-23, ZSM-35, ZSM-48, ZSM-57 and ZSM-58, with ZSM-5 being preferred.

Production of the Catalysts

The metal components of the first and second catalysts can be incorporated into the catalyst composition by co-crystallization, exchanged into the composition to the extent a Group 13 element, e.g., aluminum, is in the molecular sieve structure, impregnated therein, or mixed with the molecular sieve and binder. For example, the metal components can be impregnated in or on the molecular sieve, for example in the case of platinum, by treating the molecular sieve with a solution containing a platinum metal-containing ion. Suitable platinum compounds for impregnating the catalyst with platinum include chloroplatinic acid, platinous chloride and various compounds containing the platinum ammine complex, such as $Pt(NH_3)_4Cl_2H_2O$. Alternatively, a compound of the hydrogenation component may be added to the molecular sieve when it is being composited with a binder, or after the molecular sieve and binder have been formed into particles by extrusion or pelletizing. The second metal component may be incorporated into the catalyst composition at the same time and in the same manner as the first metal component. Alternatively, the second metal component may be incorporated into the catalyst composition after the first metal component has been incorporated, and this may be achieved in the same or an alternative manner.

After incorporation of the metal components, the molecular sieve is usually dried by heating at a temperature of 65° C. to 160° C., typically 110° C. to 143° C., for at least 1 minute and generally not longer than 24 hours, at pressures ranging from 100 to 200 kPa-a. Thereafter, the molecular sieve may be calcined in a stream of dry gas, such as air or nitrogen, at temperatures of from 260° C. to 650° C. for 1 to 20 hours. Calcination is typically conducted at pressures ranging from 100 to 300 kPa-a.

In some cases it may be desirable to steam treat and/or sulfide one of more of the catalyst beds prior to use. Steam treatment may be effected by contacting the catalyst composition with from 5 to 100% steam at a temperature of at least 260 to 650° C. for at least one hour, typically from 1 to 20 hours, at a pressure of 100 to 2590 kPa-a. Sulfiding is conveniently accomplished by contacting the catalyst with a source of sulfur, such as hydrogen sulfide, at a temperature ranging from about 320 to 480° C. for a period of about 1 to about 24 hours.

Transalkylation Process

The first and second catalyst beds and, if present, the third catalyst bed may be located in separate reactors but are conveniently located in a single reactor, typically separated from another by spacers or by inert materials, such as, alumina balls or sand. Alternatively, the first and second catalyst beds could be located in one reactor and the third catalyst bed located in a different reactor. As a further alternative, the first catalyst bed could be located in one reactor and the second and third catalyst beds located in a different reactor. In all situations, the first catalyst is not mixed with the second catalyst and the hydrocarbon feedstocks and hydrogen are arranged to contact the first catalyst bed prior to contacting the second catalyst bed. Similarly, if the third catalyst bed is present, the hydrocarbon feedstocks and hydrogen are arranged to contact the second catalyst bed prior to contacting the third catalyst bed.

In operation, the first catalyst bed is maintained under conditions effective to dealkylate aromatic hydrocarbons containing $C_2+$ alkyl groups in the heavy aromatic feedstock and to saturate the resulting $C_2+$ olefins. Suitable conditions for operation of the first catalyst bed comprise a temperature in the range of about 100 to about 800° C., preferably about 300 to about 500° C., a pressure in the range of about 790 to about 7000 kPa-a, preferably about 2170 to 3000 kPa-a, a $H_2$:HC molar ratio in the range of about 0.01 to about 20, preferably about 1 to about 10, and a WHSV in the range of about 0.01 to about 100 $hr^{-1}$, preferably about 2 to about 20 $hr^{-1}$.

The second catalyst bed is maintained under conditions effective to transalkylate $C_9+$ aromatic hydrocarbons with said at least one $C_6$-$C_7$ aromatic hydrocarbon. Suitable conditions for operation of the second catalyst bed comprise a temperature in the range of about 100 to about 800° C., preferably about 300 to about 500° C., a pressure in the range of about 790 to about 7000 kPa-a, preferably about 2170 to 3000 kPa-a, a $H_2$:HC molar ratio in the range of about 0.01 to about 20, preferably about 1 to about 10, and a WHSV in the range of about 0.01 to about 100 $hr^{-1}$, preferably about 1 to about 10 $hr^{-1}$.

Where present, the third catalyst bed is maintained under conditions effective to crack non-aromatic cyclic hydrocarbons in the effluent from the second catalyst bed. Suitable conditions for operation of the third catalyst bed comprise a temperature in the range of about 100 to about 800° C., preferably about 300 to about 500° C., a pressure in the range of about 790 to about 7000 kPa-a, preferably about 2170 to 3000 kPa-a, a $H_2$:HC molar ratio in the range of about 0.01 to about 20, preferably about 1 to about 10, and a WHSV in the range of about 0.01 to about 100 $hr^{-1}$, preferably about 1 to about 50 $hr^{-1}$.

Obviously, where the first, second and optional third catalyst beds are located in a single reactor, the operating conditions in each bed are substantially the same.

Catalyst Regeneration

As the catalyst system described above is used to transalkylate a heavy aromatic feedstock, the catalyst in each bed slowly becomes less active as coke builds up on the catalyst. In practice, this deactivation normally materializes in a gradually increasing value for the normalized average reactor temperature (NART), which is the temperature required at any point in time to achieve the design conversion at the design operating conditions. When the NART reaches a predetermined value, the present process provides for in-situ hydrogen treatment to increase the activity of the catalysts. This is effected by interrupting the supply of the feedstock and the at least one $C_6$-$C_7$ aromatic hydrocarbon, but not the supply of hydrogen, to the catalyst beds. The catalyst beds are then contacted with the hydrogen alone under conditions effective to regenerate the catalysts. Such conditions generally comprise a temperature in the range of about 365 to about 500° C., a pressure in the range of about 150 to about 6000 kPa-a, and a WHSV in the range of about 0.01 to about 10 $hr^{-1}$. After a suitable period of regeneration, such as from about 0.5 hour to about 3 weeks, normally from about 1 hour to about 24 hours, the supply of the feedstock and the at least one $C_6$-$C_7$ aromatic hydrocarbon is reinstated and transalkylation continued until further regeneration is required. These repeating periods of transalkylation and regeneration are shown in FIG. 1. Typically, the ratio of the time during which the heavy aromatic feedstock, $C_6$-$C_7$ aromatic hydrocarbon and hydrogen are supplied to the catalyst beds to effect transalkylation to the time during which hydrogen alone is supplied to the catalyst beds to effect regeneration is in the range from about 1:1 to about 500:1.

Although regular hydrogen regeneration will normally be sufficient to maintain the activity of the catalyst beds and hence the NART within an acceptable range, it may occasionally be necessary to subject one or more of the catalyst beds to oxygen regeneration to increase the useful life of the catalysts. This may require removal of the catalysts from the reactor and will typically involve contacting the or each catalyst with an oxygen-containing gas, such as air, at a temperature of about 350° C. to about 500° C. for about 0.5 hour to about 3 weeks.

The invention will now be more particularly described with reference to the Examples.

The Examples were conducted using a catalyst having the following three beds:
(1) a top bed comprising 50 wt % ZSM-5 and 50 wt % $Al_2O_3$ with 0.1 wt % Pt;
(2) a middle bed comprising 65 wt % ZSM-12 and 35 wt % $Al_2O_3$ with 0.1 wt % Pt; and
(3) a bottom bed comprising 65 wt % ZSM-5 and 35 wt % $Al_2O_3$.

The three bed catalyst was loaded into a downflow reactor in a 27:63:10 weight ratio of the top bed:middle bed:bottom bed. The reactor voids were filled with inert glass beads and 80/120 mesh quartz sand was used to fill the catalyst bed interstitial spaces.

Example 1

The fresh three bed catalyst system was used to convert a heavy aromatics stream comprising 85 wt % of a full range (including 218° C.+ boiling point tails) $C_9+$ aromatics feed blended with 8 wt % benzene and 7 wt % toluene. Reaction conditions included an initial temperature of 410° C., WHSV of 4, a hydrogen partial pressure of 182 psia (1255 kPa) and a hydrogen to hydrocarbon molar ratio of 1.

Before evaluating its performance, the catalyst was de-edged by contacting with the feed under reaction conditions for 40 days so that the aromatics ring loss was kept below 2%.

Figure 2:
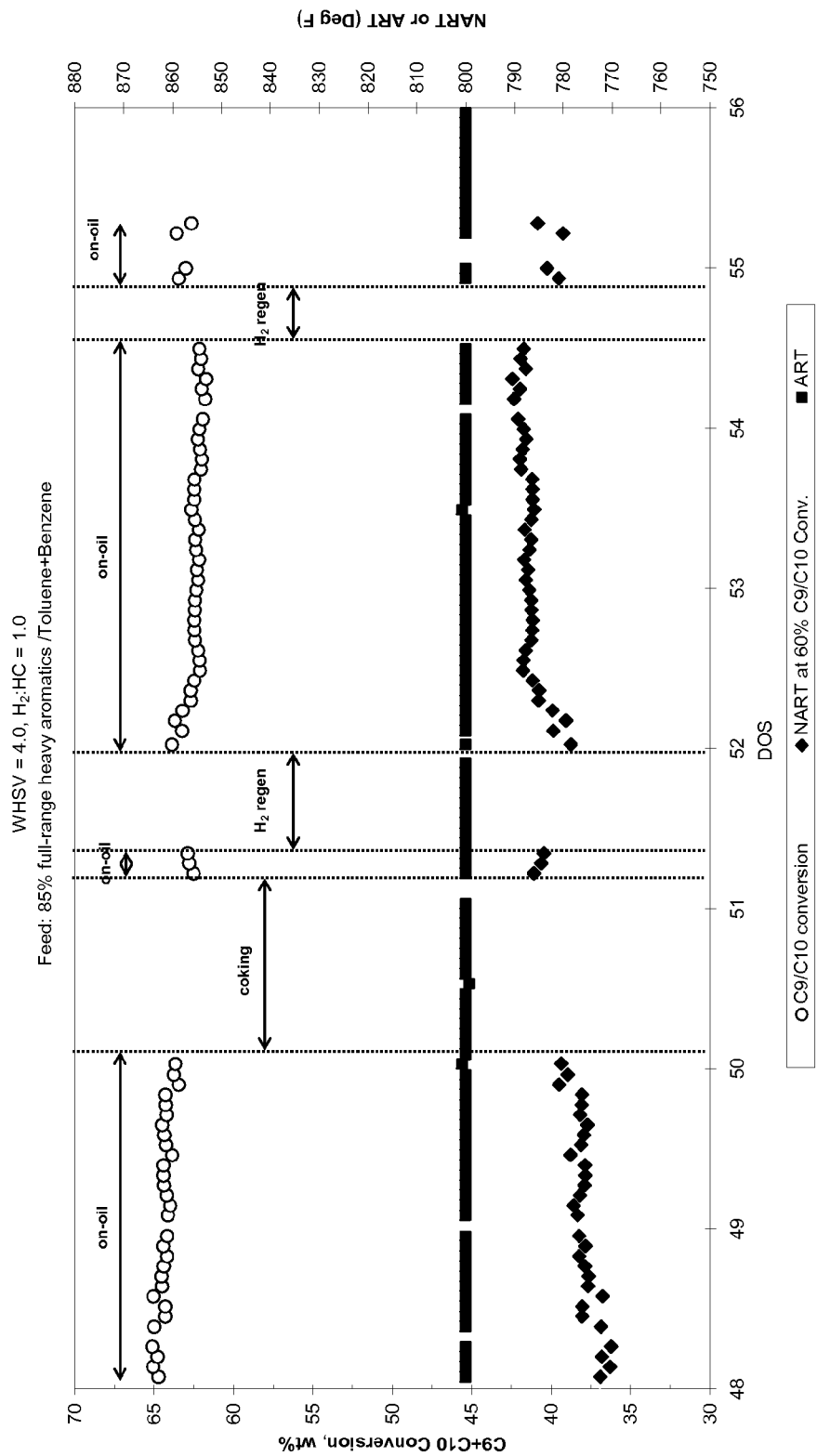
FIG. 2 is a graph of $C_9$ and $C_{10}$ conversion and NART against days on stream for the transalkylation process of Example 1.

Catalyst activity was measured by the normalized average reactor temperature (NART) required to achieve 60% conversion of the $C_9$ and $C_{10}$ aromatics in the feed. The results are plotted in FIG. 2 which shows that from day on stream (DOS) 48 to 50, the catalyst slowly deactivated as shown by the increasing NART and/or the decreasing $C_9+C_{10}$ conversion. At day 50 the hydrogen to hydrocarbon molar ratio was reduced to accelerate aging and, as a result, after only one day the $C_9+C_{10}$ conversion had decreased from 63.7% to 62.5% and the NART had increased from 780° F. (416° C.) to 786° F. (419° C.). At this point, the end of DOS 51, the supply of the hydrocarbon charge was interrupted, and hydrogen regeneration was conducted overnight. On day 52, when the unit was returned to on-oil mode, the catalyst had resumed its activity as evidenced by the NART returning to 780° F. (416° C.). From DOS 52 to 54.5 the catalyst experienced continuous slow deactivation so that the NART had increased to 788° F. (420° C.) on DOS 54.5. Then another hydrogen regeneration was performed which again successfully recovered the lost catalyst activity (NART decreased back to 780° F. (416° C.)).

Example 2

Figure 3:
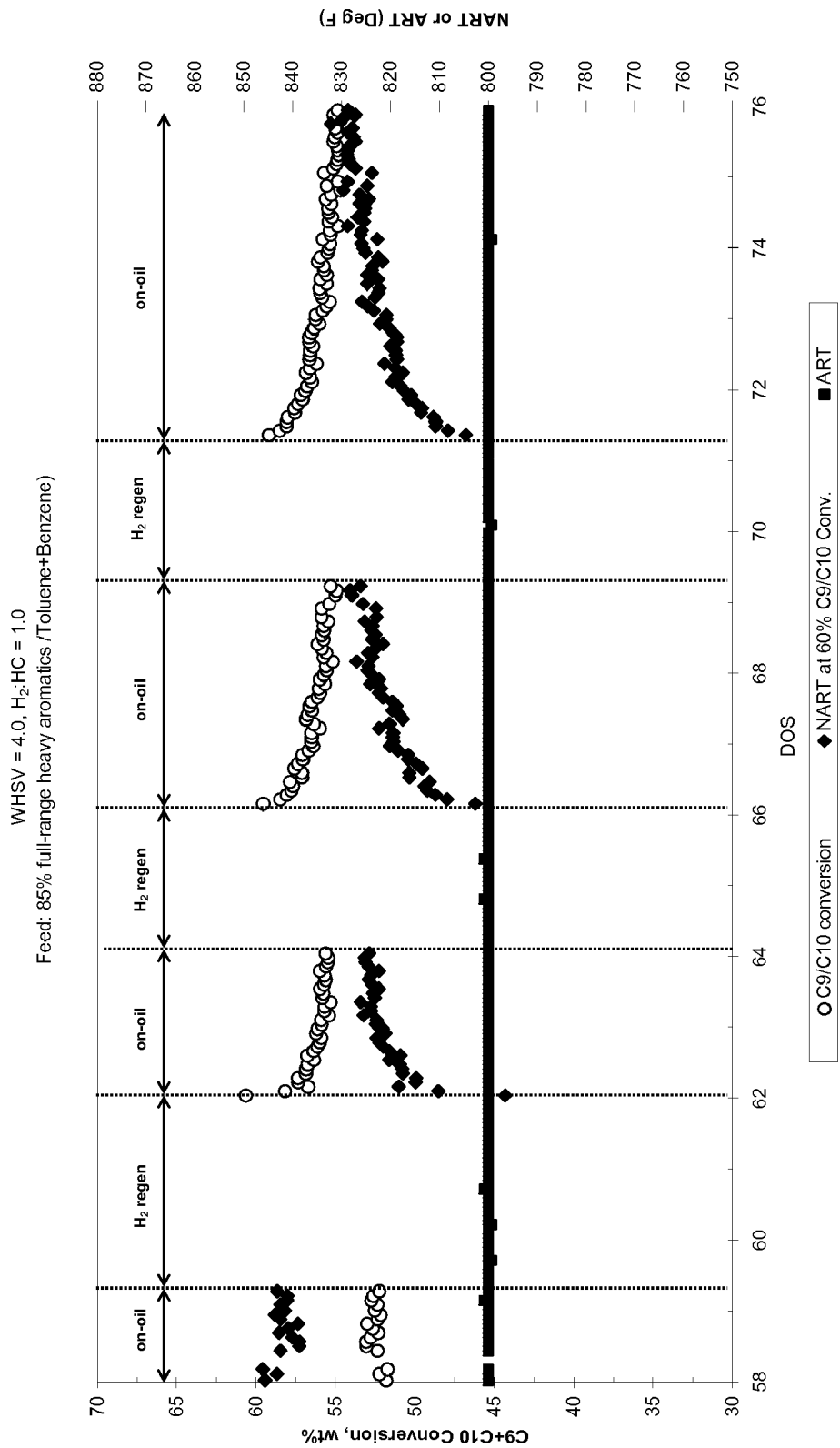
FIG. 3 is a graph of $C_9$ and $C_{10}$ conversion and NART against days on stream for the transalkylation process of Example 2.

This Example shows that the in-situ hydrogen treatment disclosed herein can also be employed to recover lost activity in a catalyst that has experienced extensive deactivation. This is demonstrated in FIG. 3 which gives the results of the continuation of the same run illustrated in FIG. 1. Before DOS 59.2, the catalyst had undergone significant deactivation as a result of severe coking induced by deliberately operating the unit at zero hydrogen partial pressure. The low catalyst activity is indicated by a high NART value of 843° F. (451° C.). At DOS 59.2 the supply of the hydrocarbon charge was interrupted, and hydrogen regeneration was conducted for over 2 days. At DOS 62, when the supply of hydrocarbon charge was reestablished, the catalyst activity had recovered by at least 30° F. (17° C.). Two subsequent $H_2$ regeneration processes were conducted, at DOS 64 and 69.2, and both demonstrated successful recovery of the lost catalyst activity.

Example 3

This Example shows that the in-situ hydrogen treatment disclosed herein can also be employed to recover lost activity in a catalyst that has undergone prior oxidative regeneration. The experiment was conducted with the catalyst employed in Example 1 after the catalyst had been oxygen regenerated by burning the coke on the spent catalyst with a diluted oxygen flow at a moderately elevated temperature (350° C.), and further at higher temperature (454° C.) with higher oxygen concentration (known as clean-up burn). The performance of the regenerated catalyst was tested using a feed comprising 60 wt % of a full range (including 218° C.+ boiling point tails) heavy aromatics ($C_9$+) composition blended with 40 wt % toluene. Transalkylation conditions included a charge supply rate of 4 WHSV, a hydrogen partial pressure of 243 psia (1675 kPa) and a hydrogen to hydrocarbon molar ratio of 2. Catalyst activity was measured by NART normalized to 45% conversion of toluene+$C_9$+$C_{10}$ hydrocarbons and the results are shown in FIG. 4.

Figure 4:
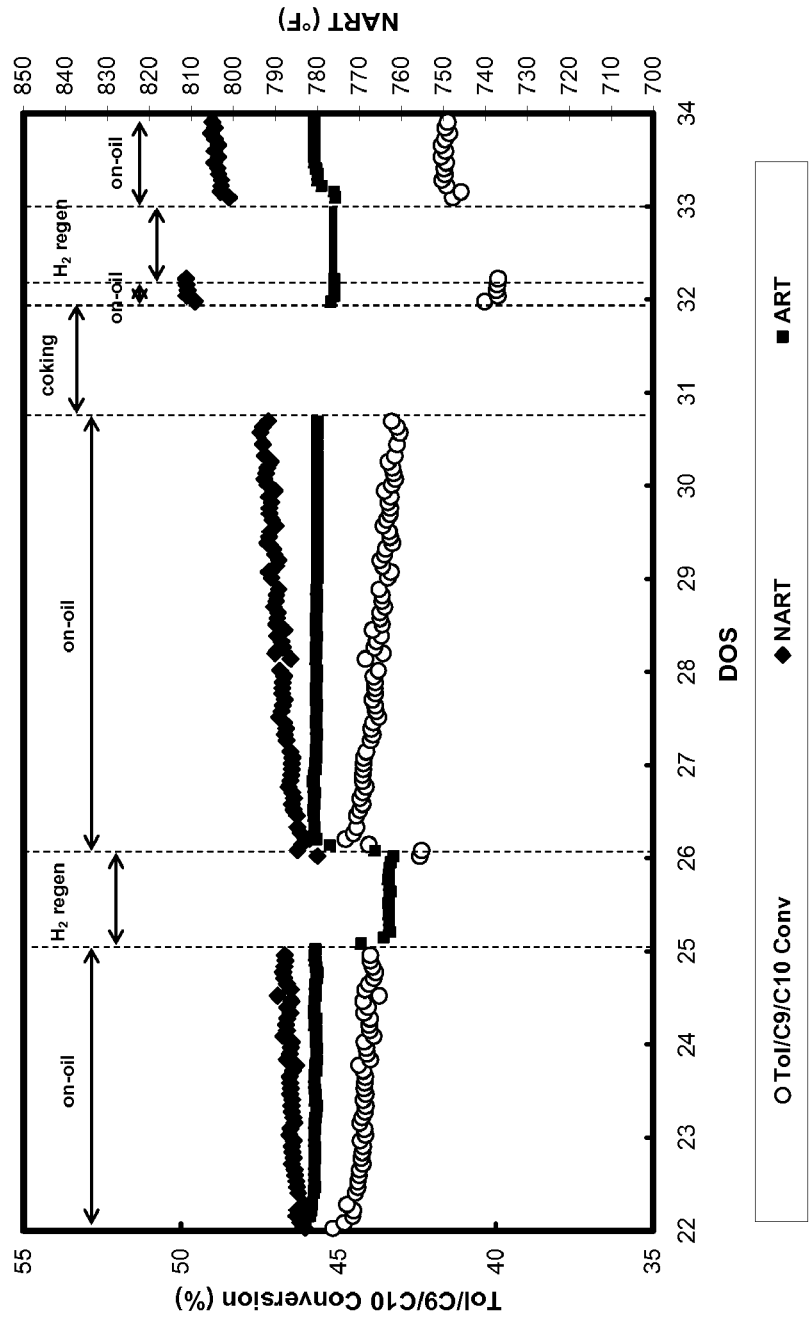
FIG. 4 is a graph of $C_9$ and $C_{10}$ conversion and NART against days on stream for the transalkylation process of Example 3.

As shown in FIG. 4, the catalyst showed decreased catalyst activity (NART=788° F. (420° C.)) on DOS 25 but, after an overnight in-situ hydrogen treatment, the activity had been restored to the same level as DOS 22 (NART=782° F. (417° C.)). Further, when coking occurred by lowering the $H_2$ partial pressure to 122 psia (841 kPa) on DOS 30.8, the catalyst activity was significantly lowered as shown by a high NART of 811° F. (433° C.). However, after in-situ hydrogen treatment for 12 hours, the NART was reduced to 801° F. (427° C.).

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing xylene by transalkylation of a $C_9$+ aromatic hydrocarbon feedstock, the process comprising:
   (a) supplying the feedstock, at least one $C_6$-$C_7$ aromatic hydrocarbon and hydrogen to at least one reaction zone containing at least first and second catalyst beds located such that the feedstock and hydrogen contact the first bed before contacting the second bed, wherein the first catalyst bed comprises a first catalyst composition comprising a molecular sieve having a Constraint Index in the range of about 3 to about 12 and at least one metal or compound thereof of Groups 6-10 of the Periodic Table of the Elements, and wherein the second catalyst bed comprises a second catalyst composition comprising a molecular sieve having a Constraint Index less than 3;
   (b) with the feedstock, $C_6$-$C_7$ aromatic hydrocarbon and hydrogen being supplied to said at least one reaction zone, operating said reaction zone(s) under a first set of conditions effective to (i) dealkylate aromatic hydrocarbons in the feedstock containing $C_2$+ alkyl groups and to saturate $C_2$+ olefins formed in the first catalyst bed and (ii) transalkylate $C_9$+ aromatic hydrocarbons with said $C_6$-$C_7$ aromatic hydrocarbon to produce xylene in the second catalyst bed; and
   (c) periodically interrupting the supply of the feedstock and said at least one $C_6$-$C_7$ aromatic hydrocarbon, but not the hydrogen, to said at least one reaction zone and contacting the first and second catalyst compositions with said hydrogen under a second set of conditions effective to enhance the activity of said first and second catalyst compositions;
   wherein said at least one metal of said first catalyst composition comprises at least one of platinum, palladium, iridium, and rhenium; and
   wherein said at least one metal is present in said first catalyst composition in an amount between about 0.01 and about 5 wt % of the catalyst composition; and
   wherein said first catalyst composition further comprises at least one further metal comprises at least one of copper, silver, gold, ruthenium, iron, tungsten, molybdenum, cobalt, nickel, tin and zinc;
   wherein said at least one further metal is present in said first catalyst composition in an amount between about 0.01 and about 1 wt % of the catalyst composition.

2. The process of claim 1, wherein said first molecular sieve comprises at least one of ZSM-5, ZSM-11, ZSM-22, ZSM-23, ZSM-35, and ZSM-48; and
   wherein said second molecular sieve comprises at least one of zeolite beta, zeolite Y, Ultrastable Y (USY), Dealuminized Y (DealY), mordenite, NU-87, ZSM-3, ZSM-4 (Mazzite), ZSM-12, ZSM-18, MCM-22, MCM-36, MCM-49, MCM-56, EMM-10, EMM-10-P and ZSM-20.

3. The process of claim 1, wherein said first molecular sieve is ZSM-5 and said second molecular sieve is ZSM-12.

4. The process of claim 3, wherein said ZSM-5 has a particle size of less than 1 micron, and said ZSM-12 has a particle size of less than 0.5 micron.

5. The process of claim 1, wherein said reaction zone contains a third catalyst bed located such that the feedstock and hydrogen in (a) and (b) contact the third bed after contacting the second bed, wherein the third catalyst bed comprises a third catalyst composition comprising a molecular sieve having a Constraint Index in the range of about 1 to about 12 and effective under said first conditions effective to crack non-aromatic cyclic hydrocarbons.

\* \* \* \* \*